United States Patent
Shabto

(10) Patent No.: US 10,610,499 B2
(45) Date of Patent: *Apr. 7, 2020

(54) OPHTHALMIC COMPOSITIONS

(71) Applicant: SaCSh Corp., Scarsdale, NY (US)

(72) Inventor: Uri Shabto, Scarsdale, NY (US)

(73) Assignee: SaCSh Corp., Scarsdale, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/587,764

(22) Filed: May 5, 2017

(65) Prior Publication Data

US 2017/0319515 A1 Nov. 9, 2017

Related U.S. Application Data

(60) Provisional application No. 62/337,571, filed on May 17, 2016, provisional application No. 62/332,789, filed on May 6, 2016.

(51) Int. Cl.

| | | |
|---|---|---|
| *A61K 31/155* | (2006.01) | |
| *A61K 47/12* | (2006.01) | |
| *A61K 9/00* | (2006.01) | |
| *A61K 9/08* | (2006.01) | |
| *A61K 31/573* | (2006.01) | |
| *A61K 47/18* | (2017.01) | |
| *A61K 47/26* | (2006.01) | |
| *A61K 47/38* | (2006.01) | |

(52) U.S. Cl.
CPC .......... *A61K 31/155* (2013.01); *A61K 9/0048* (2013.01); *A61K 9/08* (2013.01); *A61K 31/573* (2013.01); *A61K 47/12* (2013.01); *A61K 47/186* (2013.01); *A61K 47/26* (2013.01); *A61K 47/38* (2013.01); *Y02A 50/473* (2018.01)

(58) Field of Classification Search
CPC ...... A61K 31/155; A61K 31/573; A61K 9/08; A61K 47/12; A61K 47/18; A61K 47/26; A61K 47/38

See application file for complete search history.

(56) References Cited

U.S. PATENT DOCUMENTS

| | | | | |
|---|---|---|---|---|
| 5,556,848 | A * | 9/1996 | Kimura | A61K 9/0048 514/179 |
| 6,218,428 | B1 | 4/2001 | Chynn | |
| 6,872,705 | B2 | 3/2005 | Lyons | |
| 9,017,725 | B2 | 4/2015 | Mitra et al. | |
| 2005/0234018 | A1 * | 10/2005 | Lyons | A61K 9/0014 514/58 |
| 2010/0240624 | A1 * | 9/2010 | Chapin | A61K 9/0048 514/171 |
| 2013/0165419 | A1 | 6/2013 | Lindstrom et al. | |
| 2018/0147162 | A1 | 5/2018 | Shabto | |

FOREIGN PATENT DOCUMENTS

| | | | |
|---|---|---|---|
| CN | 102973925 A | * | 3/2013 |
| EP | 0807434 A1 | | 11/1997 |
| RO | 59572 A2 | | 11/1975 |
| RO | 59572 A2 | * | 3/1976 |
| WO | WO-2009006130 A2 | | 1/2009 |
| WO | WO-2013096857 A1 | | 6/2013 |
| WO | WO-2017/192944 A1 | | 11/2017 |

OTHER PUBLICATIONS

Difflam-C; Pharmacy on Web (published online 2007, http://pharmacyonweb.co.nz/difflam-anti-inflammatory-lozenge-with-cough-suppressant.html).*
Goshe et al (Cleveland Clinic Ophthalmology Update Spring 2012 pp. 1-12 Published 2012) (Year: 2012).*
Korenfeld et al J. Cataract Refract Surg vol. 35 pp. 26-34 published 2009 (Year: 2009).*
Livingstone et al., (Eye vol. 27, pp. 755-762. Published 2013). (Year: 2013).*
Goshe et al., (Cleveland Clinic Ophthalmology Spring 2012. pp. 1-12), (Year: 2012).*
Rahman et al (British J. Ophthalmology vol. 82 pp. 919-925. Published 1998) (Year: 1998).*
Goshe et al., (Cleveland Clinic Ophthalmology spring 2012). (Year: 2012).*
Rahman (British Journal Ophthamology vol. 82 pp. 919-925, 1998) (Year: 1998).*
Robaei (American Academy of Ophthalmology vol. 121 1383-1388, 2014) (Year: 2014).*
McClellan (investivative Ophthalmology and Visual Science vol. 42 pp. 2885-2893 (2001) (Year: 2001).*
ATCC Accession No. 10231.
ATCC Accession No. 16404.
ATCC Accession No. 6538.
ATCC Accession No. 8739.
ATCC Accession No. 9027.

(Continued)

*Primary Examiner* — Timothy P Thomas
*Assistant Examiner* — George W Kosturko
(74) *Attorney, Agent, or Firm* — Muriel Liberto, Esq.; Mintz Levin Cohn Ferris Glovsky and Popeo, P.C.

(57) ABSTRACT

Provided herein is an ophthalmic composition including a therapeutic active agent and an anti-inflammatory agent, in which the active agent is at least about 0.01% w/v of chlorhexidine, derivatives, or analogues of chlorhexidine, or a pharmaceutically acceptable salt, solvent, hydrate, or polymorph thereof. Methods for treating or preventing ocular disease or infection in a subject in need thereof are also provided. The method may include administering to an eye of a subject an ophthalmic composition including chlorhexidine, derivatives, or analogues of chlorhexidine, or a pharmaceutically acceptable salt, solvent, hydrate, or polymorph thereof, and an anti-inflammatory agent. The chlorhexidine, derivatives, or analogues of chlorhexidine, or a pharmaceutically acceptable salt, solvent, hydrate, or polymorph thereof and the anti-inflammatory agent are present in an amount effective to treat or prevent the ocular disease or infection in a subject in need thereof.

35 Claims, No Drawings

(56) References Cited

OTHER PUBLICATIONS

Geffen et al., Chlorhexidine gluconate 0.02% as adjunct to primary treatment for corneal bacterial ulcers. Isr Med Assoc J. Nov. 2009;11(11):664-8.
Gordon et al., The effects of topical nonsteroidal anti-inflammatory drugs on adenoviral replication. Arch Ophthalmol. Jul. 1998;116(7):900-5.
Hamill et al., Experimental evaluation of chlorhexidine gluconate for ocular antisepsis. Antimicrob Agents Chemother. Dec. 1984;26(6):793-6.
Kumar et al., Recent advances in the treatment of Acanthamoeba keratitis. Clin Infect Dis. Aug. 15, 2002;35(4):434-41.
Romanowski et al., The effects of corticosteroids of adenoviral replication. Arch Ophthalmol. May 1996;114(5):581-5.
Romanowski et al., Topical corticosteroids of limited potency promote adenovirus replication in the Ad5/NZW rabbit ocular model. Cornea. Apr. 2002;21(3):289-91.
Romanowski et al., Topical cyclosporine A inhibits subepithelial immune infiltrates but also promotes viral shedding in experimental adenovirus models. Cornea. Jan. 2005;24(1):86-91.
Seal et al., Successful medical therapy of Acanthamoeba keratitis with topical chlorhexidine and propamidine. Eye (Lond). 1996;10 ( Pt 4):413-21.
Tabor et al., Corneal damage due to eye contact with chlorhexidine gluconate. JAMA. Jan. 27, 1989;261(4):557-8.
Van Rij et al., Toxic keratopathy due to the accidental use of chlorhexidine, cetrimide and cialit. Doc Ophthalmol. 1995;90(1):7-14.
Product information sheet for chlorhexidine acetate antiseptic solution by Baxter Healthcare Ltd. Updated Sep. 13, 2016 (5 pages).
Geffen, N et al., "Chlorhexidine gluconate 0.02% as adjunct to primary treatment for corneal bacterial ulcers." *Israel Med. Assn J.* 2009, 11: 664-668.
Handbook of Pharmaceutical Excipients, 5*th* Ed. 2006, Rowe, Sheskey and Owen Editors, pp. 163-167 (Entry for Chlorhexidine) (10 pages total).
Hamill MB et al., "Experimental evaluation of chlorhexidine gluconate for ocular antisepsis." *Antimicrobiol. Agents Chemo.* 1984, 26(6):793-796.
Epstein, S et al., "Comparative toxicity of preservatives on immortalized corneal and conjunctival epithelial cells." *J. Ocular Pharmacol. Therapeutics* 2009, 25(2) 113-119.
Baudouin C, "Detrimental effects of preservatives in eyedrops: implications for the treatment of glaucoma." *Acta Ophthalmologica* 2008, 86:716-726. doi: 10.1111/j.1755-3768.2008.01250.x.
Allen LV, "Preservatives, antioxidants and pH." *Secundum Artem* May 30, 2014,18(1). (8 pages).
Pflugfelder S, "Ophthalmic preservatives: The past, present and future." Continuing Medical Education, Sponsored by the University of Florida and Candeo Clinical/Science Communications, LLC. Date of release Sep. 2008. (8 pages).

International Search Report dated Jul. 18, 2017, for PCT Application No. PCT/US2017/031211, filed May 5, 2017, 3 pages.
Written Opinion dated Jul. 18, 2017, for PCT Application No. PCT/US2017/031211, filed May 5, 2017, 6 pages.
Product information sheet for chlorhexidine irrigation solution (updated Jul. 18, 2016). Pfizer Australia (4 pages).
Wycoff, C. et al., "Prophylaxis for endopthalmitis following intravitreal injection: antisepsis and antibiotics." *Amer. J. Ophthamol.* 2011, 152(5):717-719.
Vontobel, S. et al., "Corneal penetration of polyhexamethylene biguanide and chlorhexidine digluconate." *J. Clin. Exp. Ophthamol.* 2015, 6:430-433.
Ocampo Jr., V. et al., "Toxicity of 0.2% chlorhexidine gluconate on the cornea and adjacent structures." *Phillipine J. Ophthamol.* 2005, 30(3):119-123.
Barkana, Y. et al., "Reduction of conjunctival bacterial flora by povidone iodine, ofloxacin and chlorhexidine in an outpatient setting." *Acta Ophthamol. Scand.* 2005, 83:360-363.
Montan, P. et al., "Preoperative gentamicin eye drops and chlorhexidine solution in cataract surgery." *Eur. J. Ophthamol.* 2000, 10(4): 286-292.
Merani, R. et al., "Aqueous chlorhexidine for intravitreal injection antisepsis: A case series and review." *Amer. Acad. Ophthamol.* 2016, 123(12):2588-2594.
Lin, S-C. et al., "Formulation and stability of an extemporaneous 0.02% chlorhexidine digluconate ophthalmic solution." *J. Formosan Med. Assn.* 2015, 114:1162-1169.
Carrijo-Carvalho, L. et al., "Therapeutic agents and biocides for ocular infections by free-living amoebae of *Acanthamoeba* genus." *Survey Ophthamol.* 2017, 62:203-218.
Green, K. et al., "Chlorhexidine effects on corneal epithelium and endothelium." *Arch. Ophthamol.* 1980, 98:1273-1278.
Livingstone, I. et al., "New insight into non-healing corneal ulcers: iatrogenic crystals." *Eye* 2013, 27:755-762.
Burstein, N. "Preservative cytotoxic threshold for benzalkonium chloride and chlorhexidine digluconate in cat and rabbit corneas." *Invest. Ophthamol Vis. Sci* .1980,19(3):308-312.
Browne, R. et al., "Ophthalmic response to chlorhexidine digluconate in rabbits." *Toxicol. Appl. Pharmacol.* 1975, 32:621-627.
Furrer, P. et al., "Ocular tolerance of preservatives and alternatives." *Eur. J. Pharma. Biopharma.* 2002, 53:263-280.
Ex Parte Wilhelm Heine Decision on Appeal 2018-005852 for U.S. Appl. No. 14/076,456. 8 pages.
McClellan, K. et al. (2001). "Effect of Steroids on Acanthamoeba Cysts and Trophozoites." Investigative Opthamology & Visual Science. vol. 42(12):2885-2893.
Robaei, D. et al. (2014). "The Impact of Tropical Corticosteroid Use before Diagnosis on the Outcome of Acanthamoeba Keratitis." American Academy of Ophthalmology vol. 121(7):1383-1388.
Trattler, W. et al. (2012). "Review of Ophthalmology," Second Edition, 4 pages.

* cited by examiner

OPHTHALMIC COMPOSITIONS

CROSS REFERENCE TO RELATED APPLICATIONS

This application is a non-provisional application which claims the benefit of U.S. Provisional Application No. 62/337,571, filed May 17, 2016 and U.S. Provisional Application No. 62/332,789, filed May 6, 2016, each of which is incorporated herein by reference in its entirety.

FIELD

This disclosure relates to ophthalmic compositions including chlorhexidine as an active agent and an anti-inflammatory agent, and methods for treating or preventing ocular disease or infection.

BACKGROUND

It is often difficult for a physician to determine the type of microbe causing an ocular disease or infection (e.g., conjunctivitis). Most physicians who diagnosis ocular diseases or infections (e.g., infectious conjunctivitis or corneal diseases) do not have easy access to a hospital microbiology facility to accurately diagnosis the disease. Additionally, microbiology laboratories often are not skilled in the nuances associated with identifying infections from ocular specimens. For these reasons, most conjunctivitis is not routinely cultured and is presumed to be bacterial, and is treated as bacterial infections such as with ophthalmic antibiotic solutions. However, antibiotics do not have activity against other causes of conjunctivitis including, for example, viruses and acanthamoeba, which may be misdiagnosed or undiagnosed.

There is currently a need for an ophthalmic composition for the treatment of ocular diseases or infections of at least one tissue of the eye (e.g., conjunctiva or cornea) that can potentially arise from a variety of different origins (e.g., bacterial, fungal, or viral). There is also a need for antimicrobial/anti-inflammatory combinations useful for viral, fungal, mycobacterial and amoebic infections in the post-operative period.

SUMMARY

Provided herein, inter alia, is an ophthalmic composition including a therapeutic active agent and an anti-inflammatory agent, in which the active agent is at least about 0.01% w/v of chlorhexidine, derivatives, or analogues of chlorhexidine, or a pharmaceutically acceptable salt, solvent, hydrate, or polymorph thereof.

The chlorhexidine, derivatives, or analogues of chlorhexidine, or a pharmaceutically acceptable salt, solvent, hydrate, or polymorph thereof in the ophthalmic composition may be in a concentration from about 0.01% to about 1.0% (weight/volume).

In one embodiment, the one or more anti-inflammatory agents may include a steroid or a non-steroidal anti-inflammatory agent or both. The steroid may include, for example, dexamethasone, difluprenate, fluormethalone, loteprednol etabonate, prednisolone acetate, prednisolone phosphate, or a combination thereof. For example, the anti-inflammatory may include ketotifen fumarate, diclofenac sodium, flurbiprofen sodium, ketorolac tromethamine, suprofen, celecoxib, naproxen, or rofecoxib, or a combination thereof. The anti-inflammatory agent may be in a concentration from about 0.025% to about 2% (weight/volume).

In another embodiment, the ophthalmic composition may further include a preservative. The preservative may include benzalkonium chloride, thimerosal, chlorobutanol, methyl paraben, propyl paraben, phenylethyl alcohol, edetate disodium sorbic acid, or Onamer M, or a combination thereof or a combination thereof.

In another embodiment, the ophthalmic composition may further include a pharmaceutically acceptable carrier or an ophthalmic vehicle.

In an embodiment, the ophthalmic composition may further include a co-solvent. The co-solvent may include polysorbate 20, polysorbate 60, polysorbate 80, Pluronic F-68, Pluronic F-84 Pluronic P-103, cyclodextrin, or a combination thereof. The co-solvent may be present in a concentration from about 0.01% to about 2% (weight/volume).

In another embodiment, the ophthalmic composition may further include a viscosity agent. The viscosity agent may include polyvinyl alcohol, polyvinyl pyrrolidone, methyl cellulose, hydroxy propyl methylcellulose, hydroxyethyl cellulose, carboxymethyl cellulose, or hydroxy propyl cellulose, or a combination thereof. The viscosity agent may be present in a concentration from about 0.01% to about 2% percent (weight/volume).

In another aspect, the ophthalmic composition may be formulated as a solution, suspension, semi-liquid, emulsion, ointment, cream, foam gel, powder or a controlled-release/sustain-release solution In yet another embodiment, the disclosure provides a method for treating or preventing ocular disease or infection in a subject in need thereof. The method includes administering to an eye of a subject an ophthalmic composition including a therapeutic active agent and an anti-inflammatory agent, wherein the active agent is at least about 0.01% w/v of chlorhexidine, derivatives, or analogues of chlorhexidine, or a pharmaceutically active salt, solvent, hydrate, or polymorph thereof effective to treat or prevent the ocular disease in a subject in need thereof.

In one aspect, the ophthalmic composition for treating or preventing ocular disease or infection may be formulated as a solution, suspension, semi-liquid, emulsion, ointment, cream, foam gel, powder or a controlled-release/sustain-release solution.

The ophthalmic composition may be used for the treatment of an ocular disease, which can include conjunctivitis, blepharitis, or keratitis. Additionally, the amount of ophthalmic composition may be effective in the prevention or treatment of infection following post-operative surgery. The ophthalmic composition, which includes chlorhexidine, derivatives, or analogues of chlorhexidine, or a pharmaceutically acceptable salt, solvent, hydrate, or polymorphs of chlorhexidine, derivatives, or analogues thereof and an anti-inflammatory agent, may be administered topically in about 0.001 mg/eye to about 5.0 mg/eye, or alternatively, the ophthalmic composition may be administered in an amount of about 50 µL to about 80 µL per eye.

In embodiments, the ocular disease or infection is of bacterial, mycobacterial, fungal, viral, or amoebal origin.

DETAILED DESCRIPTION

Provided herein, inter alia, are compositions and methods used for the treatment of ocular disease and infection. The ophthalmic composition includes a therapeutic agent, e.g., chlorhexidine, derivatives, or analogues of chlorhexidine, or a pharmaceutically acceptable salt, solvent, hydrate, or polymorphs of chlorhexidine, derivatives, or analogues thereof, and an anti-inflammatory agent (e.g., a steroid or a non-steroidal anti-inflammatory agent). In embodiments, the composition inhibits the viability of at least one microorganism upon application (e.g., topical application). The chlorhexidine, derivatives or analogues of chlorhexidine, or a pharmaceutically acceptable salt, solvent, hydrate, or polymorphs of chlorhexidine, derivatives, or analogues thereof may be in an amount between about 0.01% to about 1.0% w/v combined with an anti-inflammatory agent.

The methods and compositions including both chlorhexidine, derivatives, or analogues of chlorhexidine, or a pharmaceutically acceptable salt, solvent, hydrate, or polymorphs of chlorhexidine, derivatives, or analogues thereof and an anti-inflammatory agent provide significant advantages to current methods and compositions for the treatment of ocular diseases and infection. The use of chlorhexidine and anti-inflammatories each individually for the treatment of ocular disease and infection is often problematic and detrimental to the subject. For example, both minor and severe sensitivity reactions have raised concerns of the safety of chlorhexidine. In 1998, the FDA issued a Public Health Notice advising healthcare professionals of the potential for serious hypersensitivity reactions to medical devices containing chlorhexidine.

As the human eye is much more delicate than the surfaces of the skin or oral mucosa, use of chlorhexidine in the eye has been more risky and therefore limited as it is known to be an irritant to the eye. Its use as a contact lens sterilizer led to reports of eye damage when not thoroughly rinsed from the lens prior to wearing. Even in compositions wherein chlorhexidine may be included, it is often used as a disinfectant (e.g., for oral care and oral hygiene). Furthermore, in certain compositions, chlorhexidine is most often used at low concentrations (e.g., less than 0.01%) as a preservative.

Damage caused by accidental application of chlorhexidine has been reported. For example, Van Rij et al. describe accidental application of chlorhexidine to patients undergoing eye surgery causing immediate corneal edema, which led to bullous keratopathy; all affected patients required corneal transplant. See van Rij, G., et al., *Doc. Ophthalmol.* 1995; 90(1):7-14. Also, Tabor et al. similarly describe four cases when what was thought to be acceptable topical chlorhexidine accidentally got into the eyes and caused irreversible corneal damage. See Tabor, E., et al. *JAMA.* 1989 Jan. 27; 261(4):557-8. Because of its known eye toxicity, there are no readily-available commercial preparations of chlorhexidine eye drops.

The use of steroids alone is also approached cautiously in the setting of ocular infection and/or ocular disease, as steroids are known to increase susceptibility to certain infections. Topical corticosteroids are routinely used to control ocular inflammation, however, their mechanism of action involves the inhibition of the immune response and the subsequent tissue destruction that exuberant inflammation may cause. Topical steroids applied to the eye act by a variety of well described genomic and non-genomic mechanisms to reduce the production of constituent proteins of the inflammatory cascade, decrease vascular permeability, decrease the production of pro-inflammatory cytokines, decrease the potency of soluble inflammatory factors, inhibit the production of acute phase proteins, decrease leukocyte migration and increase the stability of cell membranes. Through all of these mechanisms, topically applied steroids can reduce the local concentrations of activated products toxic to the eye including the gelatinase, collaginase and matrixmetalloproteinase families of proteins. With this reduction in potentially toxic substances comes the increased risk of prolonged infection and potential infection. Caution must therefore be exercised when prescribing topical ocular steroids for potential infection as they may limit the body's ability to fight infection. Also, studies confirm both weak and potent steroids prolong viral shedding when compared to controls.

Steroids can worsen the course of an infection secondary to mycobacterial, viral, or fungal infection. In the case of *acanthamoeba* infections, this is clearly the case: multiple case reports demonstrate that erroneous pre-treatment of *acanthamoeba* eye infections correlates with worse visual outcomes. Thus, because of these significant risks, the use of a combined antimicrobial-steroid medication in ocular infections is recommended only under careful observation of a trained ophthalmologist. In fact, Tobradex® (Alcon), a combination of tobramycin and dexamethasone, the most commonly prescribed combination ophthalmic antimicrobial-steroid drug, specifically lists 'viral disease of the cornea and conjunctiva, mycobacterial infection, and fungal infection' as absolute contraindications to its use. Clearly, these combination drugs were not intended to be used for infectious conjunctivitis in which the origin of the disease is not confirmed.

This composition described herein includes a combination of chlorhexidine, derivatives, or analogues of chlorhexidine, or a pharmaceutically acceptable salt, solvent, hydrate, or polymorph thereof and an anti-inflammatory for treating, reducing, preventing and/or alleviating ocular conditions in a patient or subject in need thereof. Such ocular conditions include ocular diseases (e.g., infections of one or more tissues of the eye, the ocular conjunctiva, or the cornea) including, for example, ocular conjunctival or corneal infection caused by bacteria, mycobacteria, viruses, fungi, and amoeba. Additionally, the ophthalmic composition may also be used in the infectious prophylaxis and inflammatory control of patients following ophthalmic surgery or ophthalmic procedures, which for example, may include intraocular injections.

Definitions

Unless defined otherwise, all technical and scientific terms used herein have the meaning commonly understood by a person skilled in the art to which this disclosure belongs. The following references provide one of skill with a general definition of many of the terms used in this invention: The Cambridge Dictionary of Science and Technology (Walker ed., 1988); The Glossary of Genetics, 5th Ed., R. Rieger et. al. (eds.), Springer Verlag (1991); and Hale & Marham, The Harper Collins Dictionary of Biology (1991). As used herein, the following terms have the meanings ascribed to them below, unless specified otherwise.

Unless specifically stated or obvious from context, as used herein, the term "or" is understood to be inclusive. Unless specifically stated or obvious from context, as used herein, the terms "a", "an", and "the" are understood to be singular or plural.

Unless specifically stated or obvious from context, as used herein, the term "about" is understood as within a range of normal tolerance in the art, for example within 2 standard deviations of the mean. About can be understood as within 10%, 9%, 8%, 7%, 6%, 5%, 4%, 3%, 2%, 1%, 0.5%, 0.1%, 0.05%, or 0.01% of the stated value. Unless otherwise clear from context, all numerical values provided herein are modified by the term about.

The terms "administration" or "administering" refer to the act of providing an agent of the current embodiments or pharmaceutical composition including an agent of the current embodiments to the individual in need of treatment.

By "co-administer" it is meant that a composition described herein is administered at the same time, just prior to, or just after the administration of additional therapies. The compound or the composition of the disclosure can be administered alone or can be co-administered to the patient. Co-administration is meant to include simultaneous or sequential administration of the compound individually or in combination (more than one compound or agent). The preparations can also be combined, when desired, with other active substances.

As used herein, "sequential administration" includes that the administration of two agents (e.g., the compounds or compositions described herein) occurs separately on the same day or do not occur on a same day (e.g., occurs on consecutive days).

As used herein, "concurrent administration" includes overlapping in duration at least in part. For example, when two agents (e.g., any of the agents or class of agents described herein that has bioactivity) are administered concurrently, their administration occurs within a certain desired time. The agents' administration may begin and end on the same day. The administration of one agent can also precede the administration of a second agent by day(s) as long as both agents are taken on the same day at least once. Similarly, the administration of one agent can extend beyond the administration of a second agent as long as both agents are taken on the same day at least once. The bioactive agents/agents do not have to be taken at the same time each day to include concurrent administration.

As used herein, "intermittent administration" includes the administration of an agent for a period of time (which can be considered a "first period of administration"), followed by a time during which the agent is not taken or is taken at a lower maintenance dose (which can be considered "off-period") followed by a period during which the agent is administered again (which can be considered a "second period of administration"). Generally, during the second phase of administration, the dosage level of the agent will match that administered during the first period of administration but can be increased or decreased as medically necessary.

As used herein, an "effective amount" or "therapeutically effective amount" is that amount sufficient to affect a desired biological effect, such as beneficial results, including clinical results. As such, an "effective amount" depends upon the context in which it is being applied. An effective amount may vary according to factors known in the art, such as the disease state, age, sex, and weight of the individual being treated. Several divided doses may be administered daily or the dose may be proportionally reduced as indicated by the exigencies of the therapeutic situation. In addition, the compositions/formulations of this disclosure can be administered as frequently as necessary to achieve a therapeutic amount.

The term "anti-inflammatory agent," as used herein refers to an agent which is able to reduce inflammation in a subject. Anti-inflammatory agents can be steroidal or non-steroidal, as is known in the art.

The term "antiseptic," as used herein refers to the property of attenuating an established infection, sepsis, or putrefaction on living tissue or skin. In one embodiment, antiseptic refers to the property of being able to kill variety of microorganisms, for example one or more of bacteria, fungi, viruses, or protozoans.

The term "antimicrobial agent" refers to a substance that kills, inhibits, or prevents the growth of microbes/microorganisms such as bacteria, fungi, and viruses.

In this disclosure, "comprises," "comprising," "containing" and "having" and the like can have the meaning ascribed to them in U.S. Patent law and can mean "includes," "including," and the like; "consisting essentially of" or "consists essentially" likewise has the meaning ascribed in U.S. Patent law and the term is open-ended, allowing for the presence of more than that which is recited so long as basic or novel characteristics of that which is recited is not changed by the presence of more than that which is recited, but excludes prior art embodiments.

As used herein, the term "inflammation or inflammatory conditions of the eye" refers to an inflammatory ocular disease or any inflammatory condition of the eye and external tissues surrounding eye, e.g., infection, injury, radiation, surgery or damage to the eye or its surrounding tissues, leading to an inflammation. An inflammatory ocular disease is one caused by vascular leakage in the eye or by inflammation in the eye. Examples of conditions related to inflammation in the eye include, but are not limited to, the following: surgical trauma; dry eye; allergic conjunctivitis; viral conjunctivitis; bacterial conjunctivitis; blepharitis; anterior uveitis; injury from a chemical; radiation or thermal burn; or penetration of a foreign body, signs and symptoms of eye problems (e.g., pain in or around the eye, redness especially accompanied by pain in the eye (with or without movement), extreme light sensitivity, halos (colored circles or halos around lights), bulging (protrusion) of the eye or swelling of eye tissues, discharge, crusting or excessive tearing; eyelids stuck together, especially upon awakening, blood inside the front of the eye (on the colored part) or white of the eye); cataracts; pain and inflammation associated with wearing contact lenses; corneal conditions cornea edema after cataract surgery, corneal clouding, corneal transplantation, corneal ulcer, dry eye syndrome, dystrophies, conditions associated with excimer laser phototherapeutic keratectomy, herpes simplex keratitis, keratoconus, pterygium, recurrent erosion syndrome); eye movement disorders; glaucoma; ocular oncology, oculoplastics (e.g., cosmetic surgery, enucleation, eyelid and orbit injuries, ectropion, entropion, graves' disease, involuntary eyelid blinking); conditions associated with refractive surgery; and retinal conditions.

The term "inhibit," as used herein, means to prevent, decrease, slow-down or arrest. In one embodiment, a composition is considered to inhibit the viability of one or more microorganisms when the amount or rate of the process or reaction that takes place in the presence of the composition is decreased by at least about 10% when compared to the amount or rate in the absence of the composition. In another embodiment, a composition is considered to inhibit a process or reaction when the amount or rate of the process or reaction that takes place in the presence of the composition is decreased by at least about 20% when compared to the amount or rate in the absence of the composition. In other embodiments, a composition is considered to inhibit viability of one or more microorganisms when the amount or rate of viability that takes place in the presence of the composition is decreased by at least about 25%, about 30%, about 40%, about 50%, about 60%, about 70%, about 75% or about 80% when compared to the amount or rate in the absence of the composition. In other embodiments, a composition is considered to inhibit viability of one or more microorganisms, i.e. arresting its development.

As used herein, "microorganism" or "microbe" refers to a microscopic organism which may be single-celled or multicellular. Microorganisms can include all bacterial, archaean, and the protozoan species. This group also contains some species of fungi, algae, and certain animals. In embodiments, viruses are also classified as microorganisms.

As used herein the term "ophthalmic composition" refers to a composition intended for application to the eye or its related or surrounding tissues such as, for example, the eyelid or onto the cornea. The term also includes compositions intended to therapeutically treat conditions of the eye itself or the tissues surrounding the eye. The ophthalmic composition can be applied topically or by other techniques, known to persons skilled in the art, such as injection to the eye. Examples of suitable topical administration to the eye include administration in eye drops and by spray formulations. A further suitable topical administration route is by subconjunctival injection. The compositions can also be provided to the eye periocularly or retro-orbitally.

As used herein "pharmaceutically acceptable carrier" includes any and all solvents, dispersion media, coatings, antibacterial and antifungal agents, isotonic and absorption delaying agents, and the like that are physiologically compatible. The type of carrier can be selected based upon the intended route of administration. Pharmaceutically acceptable carriers include sterile aqueous solutions or dispersions and sterile powders for the extemporaneous preparation of sterile topical solutions or dispersion. The use of such media and agents for pharmaceutically active substances is well known in the art. Except insofar as any conventional media or agent is incompatible with the composition (e.g., chlorhexidine, derivatives, or analogues of chlorhexidine, or a pharmaceutically acceptable salt, solvent, hydrate, or polymorph thereof), use thereof in the ophthalmic compositions for the disclosure is contemplated.

As used herein, the terms "prevent," "preventing," "prevention," "prophylactic treatment" and the like refer to reducing the probability of developing a disorder or condition in a subject, who does not have, but is at risk of or susceptible to developing a disorder or condition.

Ranges provided herein are understood to be shorthand for all of the values within the range. For example, a range of 1 to 50 is understood to include any number, combination of numbers, or sub-range from the group consisting 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 as well as all intervening decimal values between the aforementioned integers such as, for example, 1.1, 1.2, 1.3, 1.4, 1.5, 1.6, 1.7, 1.8, and 1.9. With respect to sub-ranges, "nested sub-ranges" that extend from either end point of the range are specifically contemplated. For example, a nested sub-range of an exemplary range of 1 to 50 may comprise 1 to 10, 1 to 20, 1 to 30, and 1 to 40 in one direction, or 50 to 40, 50 to 30, 50 to 20, and 50 to 10 in the other direction.

By "subject" or "patient" is meant either a human or non-human animal, such as a mammal. By "subject" is meant any animal, including horses, dogs, cats, pigs, goats, rabbits, hamsters, monkeys, guinea pigs, rats, mice, lizards, snakes, sheep, cattle, fish, and birds. A human subject may be referred to as a patient.

The terms "treat," "treating" or "treatment," and other grammatical equivalents as used herein, include alleviating, abating, ameliorating, or preventing a disease, condition (e.g., conjunctivitis or other ocular diseases or infections) or symptoms, preventing additional symptoms, ameliorating or preventing the underlying metabolic causes of symptoms, inhibiting the disease or condition, e.g., arresting the development of the disease or condition, relieving the disease or condition, causing regression of the disease or condition, relieving a condition caused by the disease or condition, or stopping the symptoms of the disease or condition, and are intended to include prophylaxis. The terms further include achieving a therapeutic benefit and/or a prophylactic benefit. By therapeutic benefit is meant eradication or amelioration of the underlying disorder being treated. Also, a therapeutic benefit is achieved with the eradication or amelioration of one or more of the physiological symptoms associated with the underlying disorder such that an improvement is observed in the patient, notwithstanding that the patient may still be afflicted with the underlying disorder.

The terms "prevent," "preventing," or "prevention," and other grammatical equivalents as used herein, include to keep from developing, occur, hinder or avert a disease or condition symptoms as well as to decrease the occurrence of symptoms. The prevention may be complete (i.e., no detectable symptoms) or partial, so that fewer symptoms are observed than would likely occur absent treatment. The terms further include a prophylactic benefit. For a disease or condition to be prevented, the compositions may be administered to a patient at risk of developing a particular disease, or to a patient reporting one or more of the physiological symptoms of a disease, even though a diagnosis of this disease may not have been made.

As used herein, "viscosity" refers to a fluid's resistance to flow.

The term "weight percent" or "% (w/w)" refers to a percentage of a component in a solution that is calculated on the basis of weight for the component and the solvent. For example, a 1% (w/w) solution of a component would have 1 g of the component dissolved in a 100 g of solvent. The term "volume percent" or "% (v/v)" refers to a percentage of a component in a solution that is calculated on the basis of volume for the component and the solvent. For example, a 1% (v/v) solution of a component would have 1 ml of the component dissolved in a 100 ml of solvent. The term "weight/volume percent" or "% (w/v)" refers to a percentage of a component in a solution that is calculated on the basis of weight for the component and on the basis of volume for the solvent. For example, a 1.0% (w/v) solution of a component would have 1 g of the component dissolved in a 100 ml of solvent.

Compositions

The ophthalmic composition includes an amount of chlorhexidine, derivatives, or analogues of chlorhexidine, or a pharmaceutically acceptable salt, solvent, hydrate, or polymorph thereof, and at least one anti-inflammatory agent effective to inhibit the viability of one or more microorganisms upon application of the ophthalmic composition to an eye. In an embodiment, the ophthalmic composition is used in the treatment of an ocular disease.

Chlorhexidine

In embodiments, chlorhexidine (N,N""1,6-Hexanediylbis [N'-(4-chlorophenyl)(imidodicarbonimidic diamide)]), derivatives or analogues thereof, or pharmaceutically acceptable salts (such as, non-limiting examples, the dihydrochloride, diacetate, and digluconate), solvates, hydrates, and/or polymorphs of chlorhexidine, derivatives, or analogues thereof, is a therapeutic active agent. In embodiments of the present disclosure, the ophthalmic composition includes an active agent, e.g., chlorhexidine or derivatives or analogues thereof, or pharmaceutically acceptable salts (such as, non-limiting examples, the dihydrochloride, diacetate, and digluconate), solvates, hydrates, and/or polymorphs of chlorhexidine, derivatives, or analogues thereof.

Chlorhexidine is active, for example, against gram-positive and gram-negative organisms, facultative anaerobes, aerobes, yeasts, *acanthamoeba*, viruses and mycobacteria.

Non-limiting examples of chlorhexidine derivatives may be bisbiguanide, biguanide, guanide, aryl derivative, alkyl derivative, alicyclic derivative. For example, a chlorhexidine derivative may be N' derivatives of p-chlorophenyl biguanide, p-chlorophenyl biguanide, and p-chlorophenyl guanide.

The chlorhexidine, derivatives, or analogues of chlorhexidine, or a pharmaceutically acceptable salt, solvent, hydrate, or polymorphs of chlorhexidine, derivatives, or analogues thereof may be used in any suitable amount or concentration. In one aspect, the chlorhexidine, derivatives, or analogues of chlorhexidine, or a pharmaceutically acceptable salt, solvent, hydrate, or polymorphs of chlorhexidine, derivatives, or analogues thereof is in a concentration from about 0.01% to about 1.0% (weight/volume (w/v)) in the ophthalmic composition. In an embodiment, the chlorhexidine, derivatives, or analogues of chlorhexidine, or a pharmaceutically acceptable salt, solvent, hydrate, or polymorphs of chlorhexidine, derivatives, or analogues thereof may be in a concentration of about 0.01% (w/v) to about 0.02% (w/v); of about 0.01% (w/v) to about 0.03% (w/v); of about 0.01% (w/v) to about 0.04% (w/v); of about 0.01% (w/v) to about 0.05% (w/v); of about 0.01% (w/v) to about 0.06% (w/v); of about 0.01% (w/v) to about 0.07% (w/v); of about 0.01% (w/v) to about 0.08% (w/v); of about 0.01% (w/v) to about 0.09% (w/v); or of about 0.01% (w/v) to about 1.0% (w/v) in the composition. In an embodiment, the chlorhexidine, derivatives, or analogues of chlorhexidine, or a pharmaceutically acceptable salt, solvent, hydrate, or polymorphs of chlorhexidine, derivatives, or analogues thereof may be in a concentration of about 0.01% (w/v), about 0.02% (w/v), about 0.03% (w/v), about 0.04% (w/v); about 0.05% (w/v), about 0.06% (w/v), about 0.07% (w/v); about 0.08% (w/v), about 0.09% (w/v), or about 1.0% (w/v) in the composition.

Anti-Inflammatory Agents

In some aspects, the ophthalmic composition of the present disclosure includes one or more anti-inflammatory agents. The anti-inflammatory agent may be, for example, a steroidal anti-inflammatory agent or a non-steroidal anti-inflammatory agent. Any suitable steroidal anti-inflammatory agent or a non-steroidal anti-inflammatory agent may be included in the composition.

Non-limiting examples of steroidal anti-inflammatory agents include 21-acetoxypregnenolone, alclometasone, algestone, amcinonide, betamethosone diproprionate, budesonide, chloroprednisone, clobetasol, corticosterone, cortisone, cortivazol, deflazacort, desonide, dexamethasone alcohol, dexamethasone sodium phosphate, diflorasone, dutasteride, flumethasone pivalate, fluocinonide, fluorometholone acetate, fluorometholone alcohol, fluticasone propionate, halcinonide, halobetasol propionate, halometasone, halopredone acetate, hydrocortamate, hydrocortisone, hydroflumethiazide lotoprendol etabonate, medrysone, prednisolone acetate, prednisolone sodium phosphate, rimexolone, hydrocortisone, hydrocortisone acetate, lodoxamide tromethamine, difluprednate, or a combination thereof. In one aspect, the steroidal anti-inflammatory agent may be a corticosteroid drug such as prednisolone acetate.

Non-limiting examples of non-steroidal agents include aspirin (Anacin, Ascriptin, Bayer, Bufferin, Ecotrin, Excedrin), choline and magnesium salicylates (CMT, Tricosal, Trilisate), choline salicylate (Arthropan), celecoxib (Celebrex), diclofenac potassium (Cataflam), diclofenac sodium (Voltaren, Voltaren XR), diclofenac sodium with misoprostol (Arthrotec), diflunisal (Dolobid), etodolac (Lodine, Lodine XL), fenoprofen calcium (Nalfon), flurbiprofen (Ansaid), ibuprofen (Advil, Motrin, Motrin IB, Nuprin), indomethacin (Indocin, Indocin SR), ketoprofen (Actron, Orudis, Orudis KT, Oruvail), ketoifen fumarate, ketorolac tromethamine, magnesium salicylate (Arthritab, Bayer Select, Doan's Pills, Magan, Mobidin, Mobogesic), meclofenamate sodium (Meclomen), mefenamic acid (Ponstel), meloxicam (Mobic), nabumetone (Relafen), naproxen (Naprosyn, Naprelan), naproxen sodium (Aleve, Anaprox), oxaprozin (Daypro), piroxicam (Feldene), rofecoxib (Vioxx), salsalate (Amigesic, Anaflex 750, Disalcid, Marthritic, Mono-Gesic, Salflex, Salsitab), sodium salicylate, sulindac (Clinoril), tolmetin sodium (Tolectin), suprofen, valdecoxib (Bextra), or a combination thereof.

The anti-inflammatory agents may be used in any suitable amounts. For example, in some embodiments, such anti-inflammatory agents may be in a concentration of from about 0.025% to about 2.0% by weight. The anti-inflammatory can be present at about 0.025, about 0.05, about 0.1, about 0.2, about 0.3, about 0.4, about 0.5, about 1.0, and about 2.0 percent by weight or any amount in between these amounts. In an embodiment, the anti-inflammatory may be in a concentration of about 0.05% (w/v) to about 1.0% (w/v).

Microorganisms

In one aspect, the ophthalmic composition of the present disclosure effectively inhibits the viability of one or more microorganisms. Such microorganisms include, for example, bacteria, fungi, viruses, and protozoa. Additionally, the ophthalmic composition can inhibit the viability of two or more microorganisms (e.g., for the treatment of ocular disease and infection originating from bacterial and viral infections).

In an embodiment, the ophthalmic composition effectively inhibits the viability of one or more microorganisms, where one such microorganism includes a bacterium. Exemplary bacteria microorganisms may include both gram positive and gram negative aerobic and anaerobic bacteria. Non-limiting examples of such bacteria include *Bacillus megaterium, Enterobacter gergoviae, Aeromonas hydrophila, Aquaspirillum gracile, Nitrosovibrio tenuis, Enterobacter gergoviae, Kurthia gibsonii, Cytophaga agarovorans, Scytonema, Enterobacter gergoviae, Bacillus acidocaldarius, Cytophaga succinicans, Aquaspirillum itersonii, Azomonas insignis, Aquaspirillum aquaticum, Gardnerella vaginalis, Staphylococcus epidermis, Staphylococcus aureus, Staphylococcus hominis, Pseudomona fluorsecens, Pseudomonas facilis, Pseudomonas aeruginosa, Serratia marcescens, Propionibacterium acne, Enterococcus faecalis, Streptococcus pneumoniae, Haemophilus influenza, Escherichia coli, Moraxella catarrhalis, Mycoplasma pneumoniae, Mycobacterium tuberculosis, Mycobacterium avium, Mycobacterium gordonae* clade, *Mycobacterium kansasii* clade, *Mycobacterium nonchromogenicum/terrae* clade, Mycolactone-producing mycobacteria, *Mycobacterium simiae* clade, *Mycobacterium chelonae* clade, *Mycobacterium fortuitum* clade, *Mycobacterium parafortuitum* clade, and *Mycobacterium vaccae* clade. The composition may inhibit the viability of one or more bacteria.

In another embodiment, the ophthalmic composition of the present disclosure effectively inhibits the viability of one or more microorganisms, where one microorganism includes a fungi. Non-limiting examples of fungi include

*Candida albicans, Trichophyton mentagrophytes, Aspergillus niger, Cryptococcus neoformans, Cryptococcus gatti, Microsporum audouinii, Microsporum canis, Microsporum canis* var. *distortum, Microsporum cookei, Microsporum equinum, Microsporum ferrugineum, Microsporum flavum, Microsporum gallinae, Microsporum gypseum, Microsporum nanurn, Microsporum persicolor, Arthroderma gertleri; Arthroderma gloriae; Arthroderma gruby, Epidermophyton floccosum* and *Aspergillus fumigatus*. The composition may inhibit the viability of one or more fungi.

In another embodiment, the ophthalmic composition is capable of inhibiting the viability of one or more microorganisms, where one microorganism includes a virus. Non-limiting examples of viruses include Adenovirus, Human papillomavirus (HPV), human immunodeficiency virus-1 (HIV-1), Herpes (such as Herpes Simplex Virus-1, or Herpes zoster), Epstein-Bar virus, Polioviruses (such as Poliovirus-1), human cytomegalovirus, and varicella zoster virus. The composition may inhibit the viability of one or more viruses.

In yet another embodiment, the ophthalmic composition is capable of inhibiting the viability of one or more microorganisms, where one microorganism includes a protozoan (genus amoebae). Non-limiting examples of such protozoans include *Acanthamoeba keratitis, Trichomonas vaginalis, Leishmania major, Leishmania tropica, Leishmania aethiopica, Leishmania Mexicana* and *Leishmania (Viannia) braziliensis*. The composition may inhibit the viability of one or more protozoans.

TABLE 1

Fungi in ocular infection

| Fungi group | Fungal genus and species | Important ocular diseases |
|---|---|---|
| Hyaline filamentous | *Fusarium (F. solani, F. dimerum, F. oxysportan)* | Keratitis, scleritis, endophthalmitis |
| | *Aspergillus (A. fumigatus, A. terrus, A. terreus)* | Keratitis, scleritis, endophthalmitis, oribital cellulitis Dacryocystitis |
| | *Scedosporium (S. apiospermum, S. prolificanc)* | Keratitis, scleritis, endophthalmitis Orbital cellulitis |
| | *Paecilomyces (P. lilacinus, P. variotii)* | Keratitis, endophthalmitis |
| | *Acremonium (A. kilience, A. potronii)* | Keratitis, endophthalmitis |
| Dematiaceous | *Bipolaris (B. specifera, B. hawaiiensis)* | Keratitis, scleritis |
| | *Curvularia (C. lunata, C. geniculata)* | Keratitis, scleritis |
| | *Exserohilum (E. rostratum)* | Keratitis, scleritis |
| | *Exophiala (E. dermatitidis)* | Keratitis, scleritis |
| | *Lasiodiplodia theobromae* | Keratitis |
| Yeasts and zygomycetes | | |
| Yeasts | *Candida (C. albicans, C. parapsilosis, C. guilliermondii)* | Keratitis, infectious crystalline keratopathy, scleritis, endophthalmitis, orbital cellulitis |
| | *Cryptococcus (C. neoformans, C. laurentii)* | Keratitis, blepharitis, endophthalmitis |
| Zygomycetes | *Rhizopus, Mucor, Rhizomucor* | Orbital cellulitis, scleritis |
| Thermally dimorphic fungi | *Paracoccidioides brasiliensis, Blastomycesder matitidis, Sporothrix schenckii Histoplasma capsulatum* | Eye lid infection, conjunctivitis, keratitis, endophthalmitis |

Pharmaceutical Acceptable Carrier

The compositions herein may also include a pharmaceutical acceptable carrier or ophthalmic vehicle. The phrase "pharmaceutically acceptable carrier" or "vehicle" or "pharmaceutical vehicle" refers to a carrier for the administration of a composition (e.g., an ophthalmic composition). Exemplary carriers include saline, buffered saline, dextrose, water, glycerol, ethanol, and combinations thereof.

Co-Solvents

The ophthalmic compositions may include a co-solvent. The solubility of the components of the present compositions may be enhanced by a surfactant or other appropriate co-solvent in the composition. Such co-solvents include, but are not limited to, polysorbate 20, polysorbate 60, polysorbate 80, Pluronic F-68, Pluronic F-84 Pluronic P-103, cyclodextrin, and any other suitable agents, or a combination thereof. The co-solvents may be used in any suitable amounts. In one aspect, such co-solvents are used in a concentration of 0.01% to 2% by weight.

Preservatives

The composition may include a preservative such as an anti-microbial preservative. Suitable preservatives may include, for example, benzalkonium chloride, thimerosal, chlorobutanol, methyl paraben, propyl paraben, phenylethyl alcohol, edetate disodium sorbic acid, Onamer M Polyquat, cetyl bromide, cetyl pyridinium chloride, benzyl bromide, EDTA, phenylmercury nitrate, phenylmercury acetate, thimerosal, merthiolate, acetate and phenylmercury borate, polymyxin B sulphate, methyl and propyl parabens, quaternary ammonium chloride, sodium benzoate, sodium proprionate, and sodium perborate, and other agents known to those skilled in the art, or a combination thereof.

The preservatives may be used in any suitable amounts. In some embodiments, such preservatives are present in a concentration of about 0.001% to about 1.0% by weight. The preservative can be present at about 0.001, about 0.002, about 0.003, about 0.004, about 0.005, about 0.01, about 0.1, about 1.0% and any amount in between these amounts. In one aspect, the preservative may be included, for example, to prevent multi-dose package contamination.

Viscosity Agents

The compositions described herein may contain a viscosity agent. Any suitable agent that can increase viscosity may be used. Viscosity increased above that of simple aqueous solutions may be desirable to increase ocular absorption of the active compound, to decrease variability in dispensing the formulation, to decrease physical separation of components of a suspension or emulsion of the formulation and/or to otherwise improve the ophthalmic formulation. Such viscosity agents include, for example polyvinyl alcohol, polyvinyl pyrrolidone, methyl cellulose, hydroxy propyl methylcellulose, hydroxyethyl cellulose, carboxymethyl cellulose, hydroxy propyl cellulose, other agents known to those skilled in the art, or a combination thereof. Such agents may be used in any suitable amounts. The viscosity agents may be used in any suitable amounts. In one aspect, the viscosity agent may be employed at a level in a concentration of from about 0.01% to about 2% by weight.

pH and Buffering Capacity (e.g., Storage Conditions)

In any of the compositions of this disclosure for topical administration, such as topical administration to the eye, the compositions may be formulated in water or other aqueous solvents at a pH of about 4.5 to about 8. This pH range may be achieved by the addition of buffers to the solution.

Compounds useful as pH regulators include, but are not limited to, glycerol buffers, citrate buffers, borate buffers, acetate buffers, gluconate buffers, phosphate buffers, or citric acid-phosphate buffers may also be included.

Anesthetics

In one aspect, the compositions herein may also include an anesthetic (e.g., a pain relieving agent). Suitable pain relieving agents are local anesthetics, including, but not limited to, acetamidoeugenol, alfadolone acetate, alfaxalone, amucaine, amolanone, amylocaine, benoxinate, betoxycaine, biphenamine, bupivacaine, burethamine, butacaine, butaben, butanilicaine, buthalital, butoxycaine, carticaine, 2-chloroprocaine, cinchocaine, cocaethylene, cocaine, cyclomethycaine, dibucaine, dimethisoquin, dimethocaine, diperadon, dyclonine, ecgonidine, ecgonine, ethyl aminobenzoate, ethyl chloride, etidocaine, etoxadrol, .beta.-eucaine, euprocin, fenalcomine, fomocaine, hexobarbital, hexylcaine, hydroxydione, hydroxyprocaine, hydroxytetracaine, isobutyl p-aminobenzoate, kentamine, leucinocaine mesylate, levoxadrol, lidocaine, mepivacaine, meprylcaine, metabutoxycaine, methohexital, methyl chloride, midazolam, myrtecaine, naepaine, octacaine, orthocaine, oxethazaine, parethoxycaine, phenacaine, phencyclidine, phenol, piperocaine, piridocaine, polidocanol, pramoxine, prilocaine, procaine, propanidid, propanocaine, proparacaine, propipocaine, propofol, propoxycaine, pseudococaine, pyrrocaine, risocaine, salicyl alcohol, tetracaine, thialbarbital, thimylal, thiobutabarbital, thiopental, tolycaine, trimecaine, zolamine, and combinations thereof. Tetracaine, lidocaine and prilocaine are referred pain relieving agents herein.

Formulation

The ophthalmic composition may be in the form of a solution, a suspension, an emulsion, an ointment, a cream, a gel, or a controlled-release/sustain-release vehicle. For example, the composition may be in the form of a contact lens solution, eyewash, eyedrop, eye gel, eye ointment, and the like. The container for the compositions of the present disclosure may be clear, translucent, and opaque and may contain other properties or combination of properties such as being glass lined, tamper proof, packaged in single or few dose aliquots, and a combination thereof.

Any of the components of the composition (e.g., chlorhexidine, anti-inflammatory agent, preservatives, co-solvents, or viscosity agents) mentioned anywhere in the disclosure may be in chemically equivalent forms such as salts, hydrides, esters, and other modifications of the basic chemical. For example, prednisolone acetate in any of the compositions and methods of the disclosure may be replaced with any of its derivatives and salts thereof.

Methods

The present disclosure provides for methods of treating and/or preventing an ocular disease or infection, as discussed above, by administering the ophthalmic compositions described herein. Such ophthalmic compositions may also be useful in the infectious prophylaxis and inflammatory control of patients recovering from ophthalmic surgery. In one aspect, the present disclosure provides a method for treating and/or preventing a disease or infection described above (including, e.g., ocular disease or infection) in a subject, by administering a composition including chlorhexidine, derivatives, or analogues of chlorhexidine, or a pharmaceutically active salt, solvent, hydrate, or polymorph thereof, as an active agent and an anti-inflammatory agent to the subject, in an amount of chlorhexidine and an anti-inflammatory agent effective to treat or prevent the ocular disease or infection in a subject in need thereof.

The ophthalmic composition may be used for the treatment of an ocular disease, which can include, for example, conjunctivitis, blepharitis, or keratitis. Additionally, the amount of ophthalmic composition may be effective in the prevention or treatment of infection following post-operative surgery.

The ophthalmic composition for treating or preventing ocular disease or infection may be formulated as a solution, suspension, semi-liquid, emulsion, ointment, cream, foam gel, powder or a controlled-release/sustain-release formulation.

In forming compositions for topical administration, the compositions may be formulated as 0.01 to 2.0 percent by weight solutions in water at a pH of 4.5 to 8.0.

The compositions of the present disclosure may be administered topically on the eye. The dosage range may be about 0.001 mg to about 5.0 mg/per eye. In one aspect, the dosage for one eye may be about one drop of solution which corresponds to about 50 µl to about 80 µl of solution.

The composition may be topically applied by placing one to two drops, or more, in each eye 1 to 24 times daily. For example, the composition may be applied 1, 2, 3, 4 or 8, 12, 18 or 24 times a day, or more. In an embodiment, a composition of the present disclosure is topically applied by placing one to two drops in each eye once or twice daily.

The ophthalmic compositions can also be tested in a selected animal model. For example, a composition comprising chlorhexidine, derivatives, or analogues of chlorhexidine, or a pharmaceutically acceptable salt, solvent, hydrate, or polymorphs of chlorhexidine, derivatives, or analogues thereof and an anti-inflammatory as described herein can be used in an animal model to determine the efficacy, toxicity, or side effects of treatment with said composition. Alternatively, the composition can be used in an animal model to determine the mechanism of action of such an agent.

The disclosure has been described herein by reference to certain embodiments. However, as other variations will become apparent to those skilled in the art, the disclosure is not to be considered as limited thereto. Any compositions or methods provided herein can be combined with one or more of any of the other compositions and methods provided herein. Other features and advantages of the compositions and methods described herein will be apparent to those skilled in the art from the detailed description and claims. All patents, patent applications, and references cited anywhere are hereby incorporated by reference in their entirety.

Those skilled in the art will recognize, or be able to ascertain using no more than routine experimentation, many equivalents to the specific embodiments described herein. Such equivalents are intended to be encompassed by the following claims.

EXAMPLES

Example 1: Production of Chlorhexidine and Anti-Inflammatory Composition

Solutions of chlorhexidine and an anti-inflammatory agent were prepared using standard protocols. Briefly, excipients were added separately to pure warm (approximately 50° C.) water in an appropriately-sized container, such as a beaker. Excipients included a preservative (e.g., benzalkonium chloride), a co-solvent (e.g., polysorbate 80), an antiseptic (e.g., boric acid), and an antioxidant (e.g., ascorbic acid). The solution was stirred to allow for the incorporation of all excipients. The anti-inflammatory agent was added next. In cases where the anti-inflammatory agent is insoluble or poorly soluble in water (e.g., prednisolone acetate) the agent was wetted with the solution and then dispersed in an appropriate rheology modifier, such as a cellulose ether, e.g., METHOCEL™ E4M. The solution was mixed until it was homogenous and free of agglomeration. Chlorhexidine gluconate was then added with continuous stirring. The pH of the solution was tested and, if necessary, adjusted to approximately neutral pH (pH 7.0-7.5).

The prepared solution was transferred to appropriate sized bottles/vials (with mixing during the transfer process). The vials were crimped and sealed then autoclaved using standard sterilization techniques. If necessary, after sterilization, the vials then sonicated to break up any agglomerated material.

In a specific example, the solution contained prednisolone acetate (1%) and chlorhexidine (0.2%) with the following additives: polysorbate 80 (0.2%), boric acid (1.7%), ascorbic acid (0.1%), Methocel® E4M Premium CR (0.4%), benzalkonium chloride (1.1%).

Stability Testing

The chemical stability of chlorhexidine and prednisolone prepared as described above was evaluated at various temperatures (e.g., 5° C., 25° C., 40° C.) and relative humidity ("RH") (e.g., 25%, 40%) during 6 months of storage away from light using standard HPLC techniques. The results show that the tested solutions had acceptable stability for the chlorhexidine and prednisolone.

Prednisolone and Chlorhexidine - 6 month stability assay

| Sample | | Temp. | Humidity | Additional Impurities (%) | Results (% Remaining) |
|---|---|---|---|---|---|
| BCL592-204 (Bottle 3) | 1% Prednisolone | 40° C. | 25% | 1.29 | 107.5 |
| BCL592-204 (Bottle 2) | 1% Prednisolone, 0.2% Chlorhexidine | 40° C. | 25% | 2.87 | 106.2 91.6 |
| BCL592-204 | 1% Prednisolone, 0.2% Chlorhexidine | 5° C. | N/A | 1.23 | 102.4 115.4 |

The chemical stability of a commercial preparation of difluprednate (Durezol™) containing added chlorhexidine (0.2%) was also evaluated at various temperatures (e.g., 25° C., 40° C.) and relative humidity (e.g., 25%, 40%) during storage for 3 months using standard HPLC techniques. The results showed some loss of the difluprednate and chlorhexidine at 40° C. Similar results were seen with a commercial preparation of loteprednol etabonate (Lotemax™). It is likely that the positively charged chlorhexidine is complexing with the negatively charged rheology modifier in the commercial preparations and that this can be addressed by using a suitable non-ionic rheology modifier such as hydroxyethyl cellulose (as shown above for the prednisolone solutions).

Durezol (difluprednate) and Chlorhexidine - 3 month stability assay

| Sample | | Temperature | Humidity | Additional Impurities (%) | Results (% Remaining) |
|---|---|---|---|---|---|
| BCL601-147D | Difluprednate, Chlorhexidine | 25° C. | 40% | 16.14 | 97.0 99.3 |
| BCL601-147D | Difluprednate, Chlorhexidine | 40° C. | 25% | 16.99 | 86.7 78.6 |
| BCL601-147C | Difluprednate | 25° C. | 40% | 1.46 | 98.4 |
| BCL601-147C | Difluprednate | 40° C. | 40% | 13.89 | 96.1 |

Example 2: Antimicrobial Assays

Solutions of chlorhexidine with various anti-inflammatory agents were tested using standardized Antimicrobial Effectiveness Testing (AET), and the effectiveness as a self-preserving solution was demonstrated. The study evaluated the formulations in a neutralizer and recovery control assay in which the formulations were inoculated with 10-100 cfu of USP specified organisms, *Staphylococcus aureus*, *Pseudomonas aeruginosa*, *Escherichia coli*, *Candida albicans*, and *Aspergillus brasiliensis*. This assay is a validated method of testing for USP Antimicrobial Effectiveness.

Validation of the USP Antimicrobial Effectiveness Test (Neutralization Efficacy) was performed on two formulations of 1% Prednisolone Acetate Ophthalmic Suspension with 0.2% Chlorhexidine Gluconate. One mL of Saline-TS was added to 9 mL of DEB as a negative control (NC). One mL of product sample was added to 9 mL of DEB as sample negative controls (SNC). Each challenge organism (*S. aureus* ATCC 6538, *P. aeruginosa* ATCC 9027, *E. coli* ATCC 8739, *C. albicans* ATCC 10231, and *A. brasiliensis*, ATCC 16404) was prepared to contain a concentration between $1.0 \times 10^3$ and $1.0 \times 10^4$ cfu/mL which resulted in ≤100 cfu/mL in the inoculated tubes. A 100 µL aliquot of each challenge organism was added to 1 mL of Saline-TS and 9 mL of DEB in duplicate as positive controls (PC). A 100 µL aliquot of each challenge organism was added to 1 mL of product sample and 9 mL of DEB in duplicate as test samples (S1 and S2). Duplicate 1 mL aliquots were plated from each PC, and TS tube. The PC, and TS plates with *P. aeruginosa*, *E. coli* and *S. aureus* were poured with SCDA and incubated at 32.5° C.±2.5° C. for 3-5 days while the *C. albicans* and *A. brasiliensis* plates were poured with SDA and incubated at 22.5° C.±2.5° C. for 3-5 days (*C. albicans*) and 3-7 days (*A. brasiliensis*).

Results

TABLE 2

Test Results for 1% Prednisolone Acetate Ophthalmic Suspension with 0.2% Chlorhexidine

| Organism | Positive Control (PC) Plate Counts | Avg. PC | Test Sample Plate Counts | Avg. TS | Recovery % |
|---|---|---|---|---|---|
| *S. aureus* ATCC 6538 | 67, 79, 72, 73 | 73 | 81, 75, 78, 61 | 74 | 101 |
| *P. aeruginosa* ATCC 9027 | 63, 55, 32, 31 | 45 | 53, 61, 57, 39 | 53 | 118 |
| *E. coli* ATCC 8739 | 88, 72, 81, 80 | 80 | 91, 82, 77, 79 | 82 | 103 |
| *C. albicans* ATCC 10231 | 78, 79, 78, 76 | 78 | 89, 99, 86, 87 | 90 | 115 |
| *A. brasiliensis* ATCC 16404 | 25, 20, 27, 27 | 25 | 34, 32, 38, 36 | 35 | 140 |

TABLE 3

Test Results for Negative Controls

| | SCDA Plate Count | SDA Plate Count | Specification |
|---|---|---|---|
| Negative Control (NC) | 0 | 0 | Pass |
| Sample Negative Control (SNC) | 0 | 0 | For Information Only |

Specification: Average counts are 10-100 cfu for both PC and Test Sample and recovery percentage of Test Sample is within 50% of PC counts. No growth on the NC plates. SNC plates are for information only.
Reference: LB599-007, LB599-009

The average of the isolates recovered from the PC, and TS plates all fell between the 10-100 cfu range stipulated in SOP-00181, "USP Antimicrobial Effectiveness Testing of Category 1, 2, 3 and 4 Compendia Articles" (see Table 2 and Table 3). The average recovery from the PC tubes was at least 50% of the recovery from the TS tubes. The NC plates contained no growth. The SNC plates are for information only but also contained no growth. Based on these results, the formulation containing 1% Prednisolone Acetate Ophthalmic Suspension with 0.2% Chlorhexidine Gluconate, passed the Neutralization Efficacy Test and was validated in the Antimicrobial Effectiveness Test as defined by USP 39/NF 34. Similar formulations containing less Chlorhexidine Gluconate were also covered by this report.

I claim:

1. An ophthalmic formulation comprising chlorhexidine gluconate in an amount of from 0.05-0.20% w/v, prednisolone acetate and an ophthalmically acceptable carrier, wherein the chlorhexidine gluconate and prednisolone acetate are combined in the same formulation.

2. The ophthalmic formulation of claim 1, wherein the prednisolone acetate is at a concentration of 0.025% w/v to 2.0% w/v.

3. The ophthalmic formulation of claim 1, wherein the formulation further comprises a preservative.

4. The ophthalmic formulation of claim 3, wherein the preservative comprises benzalkonium chloride, thimerosal, chlorobutanol, methyl paraben, propyl paraben, phenylethyl alcohol, edetate disodium, sorbic acid, or a combination thereof.

5. The ophthalmic formulation of claim 1, wherein the formulation further comprises a co-solvent.

6. The ophthalmic formulation of claim 5, wherein the co-solvent comprises polysorbate 20, polysorbate 60, polysorbate 80, Pluronic F-68, Pluronic F-84 Pluronic P-103, cyclodextrin, or a combination thereof.

7. The ophthalmic formulation of claim 6, wherein the co-solvent is present in an amount of 0.01% w/v to 2.0% w/v.

8. The ophthalmic formulation of claim 1, wherein the formulation further comprises a viscosity agent.

9. The ophthalmic formulation of claim 8, wherein the viscosity agent comprises polyvinyl alcohol, polyvinyl pyrrolidone, methyl cellulose, hydroxy propyl methylcellulose, hydroxyethyl cellulose, carboxymethyl cellulose, hydroxy propyl cellulose, or a combination thereof.

10. The ophthalmic formulation of claim 9, wherein the viscosity agent is present in an amount of 0.01% w/v to 2.0% w/v.

11. A method for treating an ocular disease or infection selected from the group consisting of conjunctivitis and blepharitis in a subject in need thereof comprising administering to an eye of the subject the ophthalmic formulation of claim 1.

12. The method of claim 11, wherein the ophthalmic formulation is a solution, suspension, semi-liquid, emulsion, ointment, cream, or foam gel.

13. The method of claim 11, wherein the ophthalmic formulation is effective to treat infection following an ophthalmic surgery or an ophthalmic procedure.

14. The method of claim 11, wherein the ophthalmic formulation is administered to the eye in a concentration of 0.001 mg to 5.0 mg of the active agent per eye.

15. The method of claim 11, wherein the ophthalmic formulation is administered to the eye in an amount of 50 μL to 80 μL per eye.

16. The method of claim 11, wherein the ocular disease or infection is of bacterial, mycobacterial, fungal, viral, or amoebal origin.

17. The ophthalmic formulation of claim 1, wherein the ophthalmic formulation is a solution, suspension, semi-liquid, emulsion, ointment, cream, or foam gel.

18. The method of claim 11, wherein the prednisolone acetate is at a concentration of 0.025% w/v to 2.0% w/v.

19. The method of claim 11, wherein the ophthalmic formulation further comprises a preservative.

20. The method of claim 19, wherein the preservative comprises benzalkonium chloride, thimerosal, chlorobutanol, methyl paraben, propyl paraben, phenylethyl alcohol, edetate disodium, sorbic acid, or a combination thereof.

21. The method of claim 11, wherein the ophthalmic formulation further comprises a co-solvent.

22. The method of claim 21, wherein the co-solvent comprises polysorbate 20, polysorbate 60, polysorbate 80, Pluronic F-68, Pluronic F-84, Pluronic P-103, or cyclodextrin, or a combination thereof.

23. The method of claim 22, wherein the co-solvent is present in an amount of 0.01% w/v to 2.0% w/v.

24. The method of claim 11, wherein the ophthalmic composition formulation further comprises a viscosity agent.

25. The method of claim 24, wherein the viscosity agent comprises polyvinyl alcohol, polyvinyl pyrrolidone, methyl cellulose, hydroxy propyl methylcellulose, hydroxyethyl cellulose, carboxymethyl cellulose, or hydroxy propyl cellulose, or a combination thereof.

26. The method of claim 24, wherein the viscosity agent is present in an amount of 0.01% w/v to 2.0% w/v.

27. The ophthalmic composition of claim 1, wherein the prednisolone acetate is present in an amount of 0.05% w/v to 1.0% w/v.

28. The ophthalmic composition of claim 1, wherein the prednisolone acetate is 1.0% w/v.

29. An ophthalmic formulation comprising chlorhexidine gluconate in an amount of from 0.05-0.20% w/v, prednisolone acetate and an ophthalmically acceptable carrier, wherein the chlorhexidine gluconate and prednisolone acetate are combined in the same formulation, and wherein the formulation further comprises a co-solvent and a viscosity agent.

30. The ophthalmic formulation of claim 29, wherein the co-solvent is selected from polysorbate 20, polysorbate 60, polysorbate 80, Pluronic F-68, Pluronic F-84, Pluronic P-103, and cyclodextrin, or a combination thereof.

31. The ophthalmic formulation of claim 30, wherein the viscosity agent is selected from polyvinyl alcohol, polyvinyl pyrrolidone, methyl cellulose, hydroxy propyl methylcellulose, hydroxyethyl cellulose, carboxymethyl cellulose, and hydroxy propyl cellulose, or a combination thereof.

32. The ophthalmic formulation of claim 31, wherein the prednisolone acetate is at a concentration of 0.025% w/v to 2.0% w/v in the formulation.

33. The ophthalmic formulation of claim 32, wherein the co-solvent comprises polysorbate 80 and the viscosity agent comprises one or both of methyl cellulose and hydroxy propyl methylcellulose.

34. A method for treating an ocular disease or infection selected from the group consisting of conjunctivitis and blepharitis in a subject in need thereof comprising administering to an eye of the subject the ophthalmic formulation of claim 32.

35. The ophthalmic formulation of claim 32, wherein the co-solvent consists of polysorbate 80 and the viscosity agent consists of one or both of methyl cellulose and hydroxy propyl methylcellulose.

* * * * *